United States Patent
Street

(10) Patent No.: US 6,547,720 B1
(45) Date of Patent: Apr. 15, 2003

(54) METHOD AND APPARATUS FOR IMPROVED EYE-HAND CO-ORDINATION DURING VIDEOSCOPIC SURGERY

(76) Inventor: Graham S. B. Street, Impstone House, Pamber Road, Silchester, Reading, Berkshire (GB)

( * ) Notice: Subject to any disclaimer, the term of this patent is extended or adjusted under 35 U.S.C. 154(b) by 0 days.

(21) Appl. No.: 09/304,818

(22) Filed: May 5, 1999

(30) Foreign Application Priority Data

Mar. 18, 1999 (GB) ............................................. 9906104

(51) Int. Cl.[7] .............................................. A61B 1/04
(52) U.S. Cl. ........................... 600/111; 348/51; 600/166
(58) Field of Search ...................... 348/42–60; 600/166, 600/111

(56) References Cited

U.S. PATENT DOCUMENTS

| | | | | |
|---|---|---|---|---|
| 5,459,605 A | * | 10/1995 | Kempf | 359/462 |
| 5,488,434 A | * | 1/1996 | Jung | 348/603 |
| 5,861,713 A | * | 1/1999 | Kondo et al. | 313/467 |
| 5,936,774 A | * | 8/1999 | Street | 359/619 |

OTHER PUBLICATIONS

Taffinder et al., "The Effect of a Second–Generation 3D Endoscope on the Laproscopic Precision of Novices and Experienced Surgeons," Surgical Endoscopy, Jun. 30, 1999. 1087–1092.*

Circon 1997 Complete Product Catalog p. V–26.*

* cited by examiner

*Primary Examiner*—John M. Mulcahy
(74) *Attorney, Agent, or Firm*—Birch, Stewart, Kolasch & Birch, LLP

(57) ABSTRACT

A stereoscopic image acquisition and display system and associated method, suitable for effective eye-hand co-ordination during videoscopic surgery, is provided. The problems of previous three-dimensional acquisition and display systems are addressed by ensuring that the convergence angle for image acquisition lies within the range of 3 to 16 degrees and that the observer's visual convergence is set within similar limits. Simultaneous display of left and right eye images avoids the problems of field sequential displays. By providing the observer with a displayed image which is sufficiently bright and ensuring that the binocular disparity between corresponding points in the left and right eye images is correct, the system allows the observer to fuse a pair of stereo-images, without causing conflict between visual accommodation and convergence. The location of the displayed image may be adjusted.

12 Claims, 3 Drawing Sheets

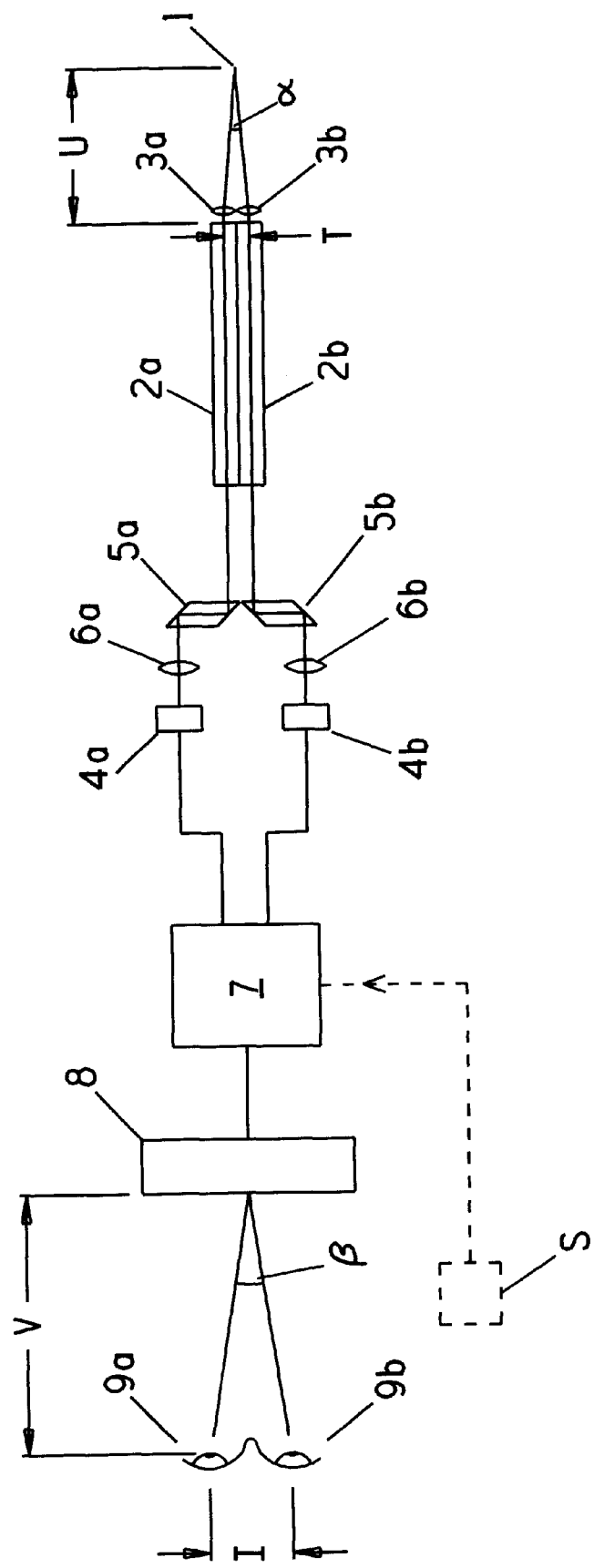
Fig. -1-

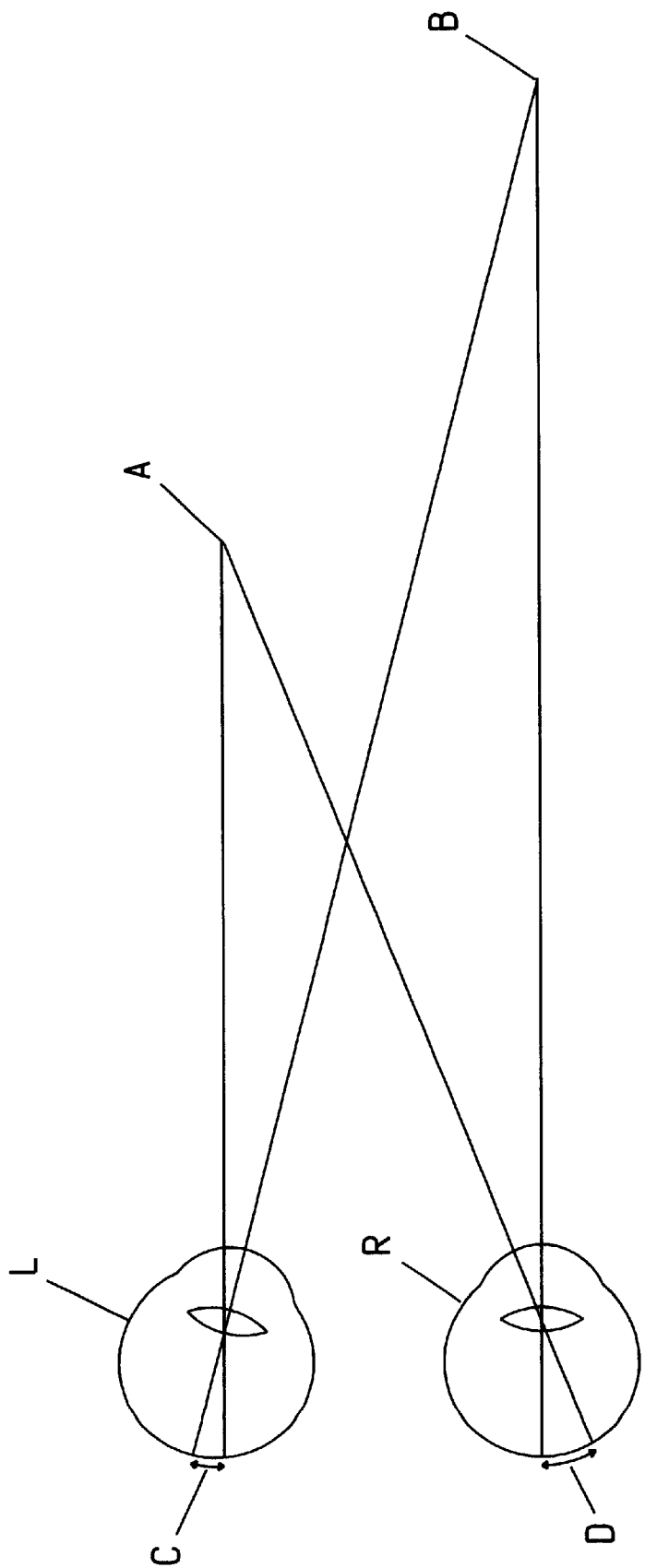
Fig. -2-

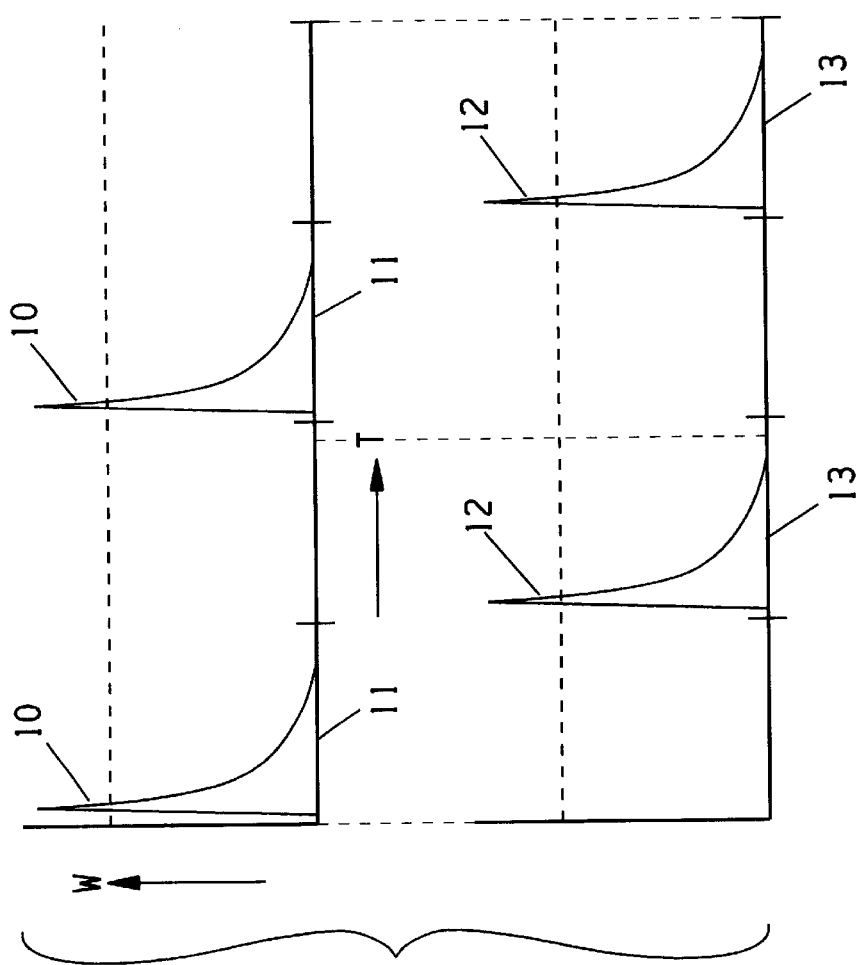
Fig. -3-

METHOD AND APPARATUS FOR IMPROVED EYE-HAND CO-ORDINATION DURING VIDEOSCOPIC SURGERY

This invention is concerned with the field of three-dimensional imaging and in particular with the provision of a natural three-dimensional image of an operative site via, inter alia, an endoscope, thereby improving the eye-hand co-ordination of a surgeon, whilst he/she carries out such a surgical procedure.

BACKGROUND

The field of Minimally Invasive Endoscopic Surgery (MIES) has, for a period in excess of 10 years, been dependent on the use of small diameter viewing devices, collectively known as endoscopes. Some of these are flexible and a majority rigid in construction. A typical working length of the insertion portion of such an instrument would be in excess of 30 cm. The diameter of this part of the instrument will typically vary from 10 mm to as low as 1 mm or less. Small diameter optics or a coherent fibre-optic bundle transfers an image of the operative site, via the distal tip of the insertion portion located inside the patient, to an external CCD camera. The image acquired in this way is displayed on a conventional television monitor placed at a comfortable viewing distance from the surgeon.

We are used to viewing live imagery on a television screen from a distance of between 6 to 12 feet. Such a screen is of considerable size and typically provides a convenient viewing window, at such a distance. Conventional television quality is sufficient to provide the definition required within this window for such passive viewing.

It has been accepted for some considerable time that a conventional two-dimensional (flat) image is a poor substitute for the natural binocular vision enjoyed by a surgeon, when carrying out an open surgical procedure. Nevertheless, the benefits to the patient, in terms of reduced trauma and scarring, and the reduced cost to the hospital, in terms of the patient's stay, have fuelled considerable growth in the MIES market, with one type of relatively simple procedure, the laparoscopic cholesystectomy, being carried out routinely, today, in this manner. Unfortunately, the handicap imposed on the surgeon's dexterity (eye-hand co-ordination) by the impaired vision provided through a conventional video image has been a brake on the migration of this technique to a variety of more complex procedures. Accordingly, the need to provide a better solution and, in particular, a three-dimensional image of the operative site has been an accepted goal, for a number of years. However, a variety of commercial attempts to address the problem, have met with poor acceptance by the surgical profession, and it has been the recognition of this reality that has provided the incentive to analyse why such first generation three-dimensional visualisation systems failed. As a result of this analysis, a second generation three-dimensional endoscopic visualisation system has been developed and this is the subject of the current invention.

In order that the scale of the problem and, thus, the significance of the improvement provided by the current invention may be fully appreciated, a summary of the analysis of the shortcomings of a typical first generation three-dimensional endoscopic system is provided here.

A typical configuration of a first generation 3D endoscopic visualisation system might include.

A TV monitor with a picture diagonal of between 14" and 20"

b) An endoscope which provides two points of view, effectively spaced a fraction of a millimetre apart at the distal tip. This may be described as a stereo-endoscope, although conventional systems have been used to achieve this to a small degree.

c) Special glasses which, when worn by the user, allow sequential viewing, respectively by left and right eye, of the two alternative perspective views of the scene, displayed sequentially on the monitor.

In use, the preferred working distance of the distal tip would be between 30 and 90 mm from the subject matter of interest, and the preferred viewing distance of the monitor would be at a conventional 2 to 3 metres from the observer. A substantial 3D effect would be observed, but, after some time, the observer would begin to feel uncomfortable and, in some cases, would suffer severe nausea. Eyestrain and headaches would be commonplace. In addition, the improvement in eye-hand co-ordination was not always as great as was expected.

In order to analyse the reasons for the effects described, it is useful to compare the nature of the binocular imagery provided to the observer by such a first generation system with that which would be experienced in a direct vision situation, and, in particular, when such a situation involves the manipulation of surgical instruments.

Historically there have been a number of factors which have created problems. These included:

1) The image acquisition geometry of the stereo-endoscope failed to adequately match the observer's viewing geometry;

2) The left and right eye images were displayed field sequentially, and not simultaneously as would be the case for natural vision;

3) The stereo-monitor displayed an image intended to aid eye-hand co-ordination, but this was not presented at a viewing distance, typically arm's length, where we would normally expect to find an object which we are manipulating;

4) The brightness of the image displayed was compromised, as a result of the field sequential display process.

It is a tenet of the current invention that the optimal solution for providing a more natural three-dimensional image, suitable for effective eye-hand co-ordination, will include the avoidance or substantial reduction of all of the above issues.

On an individual basis, some of the above problems are addressed within the prior art. For instance, in U.S. Pat. No. 5,712,732 (Street) apparatus is described in which two two-dimensional perspective images, provided by conventional liquid crystal display (LCD) panels, are combined with the aid of a semi-transparent mirror, so that each eye of the observer sees a different perspective, but in the same location. This causes the brain to fuse these perspectives into one three-dimensional image. Observer tracking ensures that each eye only sees the image intended for it. The principal purpose of the aforementioned invention is to avoid the need for the observer to wear special spectacles. Furthermore, it is normal for direct view LCD's to be provided with a polarising layer on the side viewed by the observer. The direction of polarisation of this sheet of material is normally set at 45° to the vertical. The use of a polarising element in front of each of two displays positioned mirror-symmetrically, either side of a semi-transparent mirror, is well known from the prior art. One such reference may be found on pages 365–366 of "Three-Dimensional Imaging Techniques" by Okoshi and published in 1976 by Academic Press Inc. By using suitably polarised spectacles, the viewer may therefore observe a stereoscopic or three-dimensional image. In both of these examples the observer is provided with left and right eye images, simultaneously. In International Patent Application PCT/GB97/00766 (Street) the problem of barrel distortion, encountered when using wide angle optics, is identified as causing undesirable (for instance vertical) disparity errors in a twin axis stereo-endoscope. The inventive step of PCT/GB97/00766 is to compensate for this problem by matching the distortions of both optical channels so that this effect is minimised.

SUMMARY OF THE INVENTION

It is an object of the current invention to provide a vision system which enables an observer to relate to an object field through a three-dimensional image scaled in proportion to said object field, so as to provide an environment for comfortable eye-hand co-ordination. More specifically, the invention is intended to provide a generalised method for improving eye-hand co-ordination, during videoscopic surgery.

It is a further object of the invention to provide the three-dimensional image substantially free from binocular disparity between corresponding points which would not be observed were the object field to be viewed directly.

It is also an object of the invention to provide the observer with both left and right eye images simultaneously, in order to more effectively simulate the conditions of normal binocular viewing of an object field.

It is another object of the invention to minimise the conflict between accommodation and convergence by providing suitable viewing conditions for the observer.

Thus according to the invention, a system for relaying a three-dimensional view of an object field to an observer comprises:

means for acquiring a first image of the object field from a first viewpoint and a second image of the object field from a second viewpoint, in which the viewpoints are spaced, so that, in use, a line joining the viewpoints subtends a first angle at an object point within the object field, the first angle lying within a range of three degrees to sixteen degrees;

means for displaying an image of the object point within an image field, said display means being arranged to present simultaneously at a plane a first relayed image of the object field acquired from the first viewpoint for viewing by the left eye of the observer and co-located at the plane a second relayed image of the object field acquired from the second viewpoint for viewing by the right eye of the observer; and means for positioning the plane at a distance from the observer so that, in use, a line joining the two eyes of the observer subtends a second angle at a point on the plane which lies in the range of three degrees to sixteen degrees.

Preferably said display means includes a liquid crystal display.

Advantageously, the ratio of the first angle and the second angle lies within the range 0.5 to 2.

The positioning means may include an articulated arm.

The display means can include a manual adjustment such that the brightness of the image displayed may be adjusted to be substantially equal to or exceed that of the surrounding environment.

Optionally, the system may comprise:

a sensor for sensing ambient light in the vicinity of said display means; and control means responsive to said sensor for controlling the brightness of the image displayed by said display means.

Advantageously, in use, peak white within the image viewed has a luminance in excess of 200 candela per square metre, whereby dilation of the pupil of each of the observer's eyes is limited, the observer retains a good depth of field and conflict between accommodation and convergence for a stereoscopic image is mitigated and/or avoided.

Preferably, the peak white has a luminance in the range of 250 to 700 candela per square metre.

According to another aspect of the invention, in use and at the plane, for any point within the first relayed image which has a corresponding point within the second relayed image, the vertical component of the line joining said point within the first relayed image to said corresponding point within the second relayed image subtends a third angle at the observer which does not exceed 0.5 degrees. Preferably, the third angle does not exceed 0.1 degrees.

According to the invention, a method for relaying a three-dimensional view of an object field to an observer comprises:

spacing a first and a second viewpoint so that a line joining the viewpoints subtends a first angle at an object point within the object field, the first angle lying within a range of three degrees to sixteen degrees;

acquiring a first image of the object field from the first viewpoint and a second image of the object field from the second viewpoint;

simultaneously displaying at a plane a first relayed image of the object field acquired from the first viewpoint for viewing by the left eye of the observer and, co-located at the plane, a second relayed image of the object field acquired from the second viewpoint for viewing by the right eye of the observer; and positioning the plane at a distance from the observer so that, in use, a line joining the two eyes of the observer subtends a second angle at a point on the plane which lies in the range of three degrees to sixteen degrees.

Advantageously, the ratio of the first angle and the second angle lies within the range 0.5 to 2.

Preferably, the method further comprises:

adjusting the brightness of the image displayed to be substantially equal to or greater than that of the environment.

Advantageously, the brightness is adjusted to exceed 200 candela per square metre. It may be adjusted or controlled to fall within the range of 250 to 700 candela per square metre.

Further scope of applicability of the present invention will become apparent from the detailed description given herein after. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF DRAWINGS

The present invention will become more filly understood from the detailed description given hereinbelow and the accompanying drawings which are given by way of illustration only, and thus are not limitative of the present invention, and wherein:

FIG. 1 is a diagram of a stereo-endoscopic system embodying the invention;

FIG. 2 is a diagram illustrating the effect of binocular disparity, the vertical component of which the invention seeks to minimise and the horizontal component of which the invention seeks to provide at the correct level for natural eye-hand co-ordination; and FIG. 3 graphically illustrates the variation of light levels received by each of an observer's eyes from a field sequential stereoscopic display, a characteristic which the invention seeks to address in order to more accurately mimic the nature of direct vision.

DESCRIPTION OF PREFERRED EMBODIMENTS

Referring to FIG. 1 there is shown a stereo-endoscope for viewing a point 1 within an object field. The endoscope comprises a pair of optical relay channels 2a, 2b which receive light from the object field, via respective objective lenses 3a, 3b. Each relay channel may comprise coherent fibre optic bundles or a series of relay lenses, in order to relay an image of the object field from the distal end of the channel to its viewing end. Channels 2a, 2b provide respectively for left and right eye views and transmit light to respective CCD cameras 4a, 4b, via prisms 5a, 5b and lenses 6a, 6b. An electronics system 7 takes the camera signals and provides output to a display unit 8, which comprises a back-lit LCD screen and a lenticular array arrangement capable of providing simultaneous co-located and different views of the object field directed to the left and right eyes 9a, 9b of an observer.

At the distal end of the endoscope an angle a is subtended at point 1 by the spacing of the objective lenses 3a, 3b. Within a typical range of operation, for example, the distance U from the lenses 3a, 3b to the object point is 60 mm and, with a lens spacing T of 4 mm, this sets the angle $\alpha$ to be 3.8°. As far as the observer is concerned, a typical inter-ocular distance I is 65 mm. If, for example, the distance V from the observer to the display screen 8 is 97.5 cm, then the angle $\beta$ subtended at the display by the eye spacing is also 3.8°. Such identity between $\alpha$ and $\beta$ is ideal, physiologically, in providing a realistic image, correctly scaled in terms of depth perception. In practice, the angles $\alpha$ and $\beta$ can differ within certain limits, before there is an undesirable effect on the observer's perception of depth and it has been determined that a ratio between these two angles of up to about five is acceptable. Thus, in practice, if $\alpha$ is 3°, $\beta$ can range between 3° and 16°. Similarly if $\beta$ is 3°, $\alpha$ can range between 3° and 16°. It is important to note that $\alpha$ and $\beta$ are key parameters for good eye-hand co-ordination and that the convergence angle both for the acquisition geometry and for the viewing geometry should be in the range quoted. This range is directly calculable from the range of eye-to-hand distances involved, when objects are manipulated by hand. Preferably, for the most natural appearance of the relayed image, either $\alpha$ or $\beta$ should have a value between one half and two times that of the other. Clearly, the optimum working distance U of the endoscope can be changed and the spacing T of lenses 3a, 3b adjusted accordingly. To ensure that the displayed image is located at the correct distance from the observer to meet the above criteria, it is found to be convenient to mount the display monitor at the end of an articulated, counterbalanced arm. Such an arm is standard equipment and, in this description, may be considered to form part of display unit 8. This arrangement allows the user to position the display at, for example, arms length, at which distance, all the criteria for effective eye-hand co-ordination can be met.

Referring now to FIG. 2, there is illustrated the feature of binocular disparity. When an observer views two objects A, B within one field with both eyes L, R and the objects are located at different distances, the retinal separations (C on one retina and D on the other retina) between the image points, corresponding to objects A and B, are different. This effect is called binocular disparity and it must relate correctly to the distances at which the objects are located. Furthermore, for good three-dimensional viewing, the only displacements (parallax) between corresponding points in the two images, intended for left and right eye respectively, should be along a horizontal line (in the plane of FIG. 2). Vertical displacements (perpendicular to the plane of FIG. 2) are unnatural and should be minimised. In practice, it is found that a vertical displacement between two corresponding points, which subtends an angle at the eye of less than 0.5°, can be tolerated, and that a vertical displacement of 0.1° or less is completely acceptable.

FIG. 3 illustrates the temporal characteristic of a field-sequential stereoscopic display, in which the left and right eye images are presented, in an interleaved manner, on alternate fields, rather than simultaneously, as would be the case for natural direct vision. The light received by each eye is shown separately as a function of time T, for a CRT based display system, in which the observer receives left eye information 10, during the odd fields 11, and right eye information 12, during the even fields 13. The fast rise time for each signal and subsequent decay thereof is typical for a phosphor based display. It should be noted that there are two unnatural consequences which follow from the use of such display technology. The first is the fact that CRT based solutions, unless utilising long persistence phosphors, which give rise to problems of a different kind, place an unnatural demand on the visual system and, in principle, on the fusion process, because the imagery comprises rapid, full amplitude, modulation. The second is that, for a stereoscopic field-sequential system, where image fusion is a key requirement, the intensity peaks reaching the left eye are completely out of phase with those reaching the right eye. Whilst the degree of discomfort that this causes has not been quantified, it has been found that a stereo monitor, implemented using LCD's, in which both eyes receive light simultaneously and (illustrated by the broken lines in FIG. 3) without the modulation typical of a CRT, provides an image with temporal parameters far closer to those of direct vision and substantially no discomfort reported.

A further difficulty associated with CRT based field-sequential systems, is the need to polarise the image and to further halve the duty cycle of the display, for each eye. Given other efficiency limitations of such modulation techniques, this will typically result in a reduction of at least a factor of five in the maximum brightness, which the display system can provide. The size of the eye's pupil adapts to the brightness of the scene being viewed; the darker the displayed image, the larger the pupil will be. If the ambient light levels are higher than the brightness of the displayed image, pupil size will need to adapt, every time the observer looks away from and, more importantly, when the observer's gaze is redirected towards the displayed image. If the change in pupil diameter is substantial, this will cause eye strain. In order to avoid the problem and the constraint of needing to subdue the ambient light levels, during a surgical procedure, the display system's brightness should be relatively high and adjustable, to be similar to that of the surroundings.

In practice, a brightness adjustment to allow the displayed brightness to slightly exceed that of the immediate surroundings is found to be useful. Specifically, this is related to another effect, which is a consequence of the way in which the human physiology of vision develops, from birth There is an involuntary linkage between the visual convergence angle, that between the optical axes of the left and right eye, and the shortening or lengthening of the focal length of each eye's lens, in order to accomnmodate the longer or shorter focal distance required to provide a sharp image of that part of the object field, at which the eyes are converged. Since the display technology used, in a majority of three-dimensional display systems, will typically have a real or virtual image plane, at which the image for each eye is actually formed, the distance at which this is located will, for all corresponding points with a non-zero parallax, be different to that indicated by the eyes' convergence. Each eye's lens will accordingly tend to adopt a focal length which may not accord with the distance at which the display plane is located. This accommodation-convergence conflict may be substantially alleviated, by providing the image displayed with sufficient brightness, thereby preventing unwanted pupil dilation and associated reduction in each eye's depth of field. In this way, inferred distances within the image displayed will fall within this depth of field and image detail will not be degraded. Experiment has shown that a displayed brightness of over 200 and preferably in the range of 250 to 700 candela per square metre for a white object, within the object field and displayed as a fill amplitude or peak white signal on the display, is sufficient to achieve this objective. This is typically not achieved by conventional stereo-display monitors, where image brightness is normally found to be less than 70 candela per square metre. Brightness may be set manually with controls provided on display unit 8 or automatically by electronics system 7.

It will be clear, to those versed in the art, that a number of different arrangements of components can adhere, in general, to the teachings of this invention. For instance two LCD panels, each provided with a very bright back light and the images from which are viewed in combination with the aid of a beam combining, semi-transparent mirror, as shown in U.S. Pat. No. 5,712,732 (Street), could meet the brightness criteria outlined above. This could also be true for CRT based systems, provided very bright phosphors are used. However, in order to avoid loss of image definition, high voltages may be required. A single LCD screen, as assumed in the embodiment of FIG. 1 and arranged in accordance with PCT/GB96103014 (Street), provided with a bright back light can also meet the requirements of the current invention. Other display technologies, such as the light valve technology used for projected images, would be suitable, if these are arranged to provide a stereo image of sufficient brightness, in such a way that it also meets the geometric criteria for image acquisition and display, outlined herein and required for good eye-hand co-ordination Whilst the embodiment of FIG. 1 described above assumes a manual adjustment for display brightness, it would be a routine matter to sense the ambient light level using a sensor S, located in the vicinity of the display and the observer, and for the electronics system 7 to make an automatic adjustment. This modification is considered optional, as indicated by the dashed lines in FIG. 1. Although the description has illustrated display means which is viewed directly, it may be convenient to view the displayed image as a virtual image, for instance, with the aid of a mirror. It may also be convenient to relay an image of the displayed image using a lens system or one or more curved mirrors, whilst retaining the required characteristics of the viewed image, and its spatial relationship, with respect to the observer.

The invention being thus described, it rill be obvious that the same may be varied in many ways. Such variations are not to be regarded as departure from the spirit and scope of the invention, and all such modifications as would be obvious to one skilled in the art are intended to be included within the scope of the following claims.

What is claimed is:

1. A method for relaying a three-dimensional view of an object field to an observer comprising:
   spacing a first and a second viewpoint so that a line joining the viewpoints subtends a first angle at an object point within the object field, the first angle lying within a range of three degrees to sixteen degrees;
   acquiring a first image of the object field from the first viewpoint and a second image of the object field from the second viewpoint;
   simultaneously displaying at a plane a first relayed image of the object field acquired from the first viewpoint for viewing by the left eye of the observer and, co-located at the plane, a second relayed image of the object field acquired from the second viewpoint for viewing by the right eye of the observer; and
   positioning the plane at a distance from the observer so that, in use, a line joining the two eyes of the observer subtends a second angle at a point on the plane which lies in the range of three degrees to sixteen degrees.

2. A method as claimed in claim 1 in which the ratio of the first angle and the second angle lies within the range 0.5 to 2.

3. A method as claimed in claim 1 further comprising:
   adjusting the brightness of the image displayed to be substantially equal to or greater than that of the environment.

4. A method as claimed in claim 1 wherein the brightness of the image displayed is adjusted to exceed 200 candela per square metre.

5. A method as claimed in claim 4, wherein the brightness is adjusted to fall within the range of 250 to 700 candela per square metre.

6. A method as claimed in claim 1 further comprising:
   positioning the plane by means of an articulated arm.

7. A method as claimed in claim 1 further comprising:
   providing a sensor for sensing ambient light in the vicinity of the plane; and
   controlling in response to the signal from said sensor the brightness of the image displayed at the plane.

8. A method as claimed in claim 1 further comprising:
   arranging, at the plane, for a point within the first relayed image to have a corresponding point within the second relayed image, so that the vertical component of the line joining said point within the first relayed image to said corresponding point within the second relayed image subtends a third angle at the observer which does not exceed 0.5 degrees.

9. A method as claimed in claim 8 in which the third angle does not exceed 0.1 degrees.

10. A method for relaying a three-dimensional view of an operative field to an observer during a surgical procedure carried out by said observer comprising:
    spacing a first and a second viewpoint so that a line joining the viewpoints subtends a first angle at an operative point within the operative field, the first angle lying within a range of three degrees to sixteen degrees;

acquiring a first image of the operative field from the first viewpoint and a second image of the operative field from the second viewpoint;

simultaneously displaying at a plane a first relayed image of the operative field acquired from the first viewpoint for viewing by the left eye of the observer and, co-located at the plane, a second relayed image of the operative field acquired from the second viewpoint for viewing by the right eye of the observer;

positioning the plane at a distance from the observer so that, in use, a line joining the two eyes of the observer subtends a second angle at a point on the plane which lies in the range of three degrees to sixteen degrees; and adjusting the brightness of the first and second images to exceed 200 candela per square meter.

11. A method as claimed in claim 10 in which the ratio of the first angle and the second angle lies within the range 0.5 to 2.

12. A method as claimed in claim 10, wherein the brightness is adjusted to fall within the range of 250 to 700 candela per square meter.

* * * * *